United States Patent [19]
Martin et al.

[11] Patent Number: 5,936,116
[45] Date of Patent: Aug. 10, 1999

[54] PREPARATION OF ALLYL SUCCINATE DERIVATIVES AND STARTING MATERIALS THEREFOR

[75] Inventors: Fionna Mitchell Martin; Christopher Norman Lewis; Stephen Arthur Bowles; Richard Simon Todd, all of Oxford, United Kingdom

[73] Assignee: British Biotech Pharmaceuticals Limited, Oxford, United Kingdom

[21] Appl. No.: 09/068,673

[22] PCT Filed: Nov. 18, 1996

[86] PCT No.: PCT/GB96/02531

§ 371 Date: May 14, 1998

§ 102(e) Date: May 14, 1998

[87] PCT Pub. No.: WO97/18183

PCT Pub. Date: May 22, 1997

[30] Foreign Application Priority Data

Nov. 16, 1995 [GB] United Kingdom .................. 9523493

[51] Int. Cl.[6] .......................... C07C 67/00; C07C 69/74; C07C 69/34
[52] U.S. Cl. .............................. 560/190; 560/96; 560/127
[58] Field of Search ...................... 560/179, 205, 560/96, 127, 190

[56] References Cited

U.S. PATENT DOCUMENTS

4,939,288  7/1990  Talley ........................................ 560/81

*Primary Examiner*—Gary Geist
*Assistant Examiner*—Taylor Victor Oh
*Attorney, Agent, or Firm*—Banner & Witcoff, Ltd.

[57] ABSTRACT

A process for the preparation of a compound of formula (I) wherein $R_2$ is a $(C_1-C_6)$alkyl, $(C_2-C_6)$alkenyl, $(C_2-C_6)$alkynyl, phenyl$(C_1-C_6)$alkyl, heteroaryl$(C_1-C_6)$alkyl, cycloalkyl$(C_1-C_6)$alkyl or cycloalkenyl$(C_1-C_6)$alkyl group, any one of which may be optionally substituted by one or more substituents selected from $(C_1-C_6)$alkyl, $(C_1-C_6)$alkyl, —S$(C_1-C_6)$alkyl, halo and cyano (—CN); and $R_7$ is a carboxylic acid protecting group, which process comprises the internal molecular rearrangement of an allyl carboxylate compound of formula (II) wherein $R_2$ and $R_7$ are as defined in relation to formula (I) to form the desired compound of formula (I). Compounds (I) are intermediates for the preparation of Matrix metaloproteinase inhibitors.

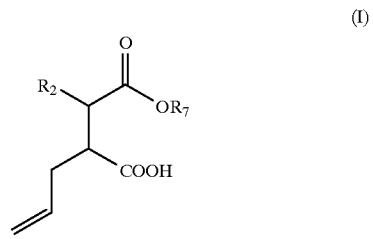

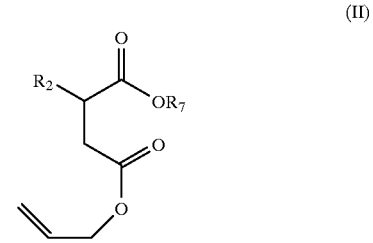

9 Claims, No Drawings

PREPARATION OF ALLYL SUCCINATE DERIVATIVES AND STARTING MATERIALS THEREFOR

This invention relates to the preparation of 4-carboxy-protected, optionally 3-substituted, 2-allyl-succinates. Such compounds are useful as intermediates in the preparation of known inhibitors of matrix metalloproteinases.

BACKGROUND TO THE INVENTION

Compounds which have the property of inhibiting the action of metalloproteinases involved in connective tissue breakdown such as the collagenases, stromelysins, gelatinases and matrilysin (known as "matrix metalloproteinases", and herein referred to as MMPs) are considered potentially useful for the treatment or prophylaxis of conditions involving such tissue breakdown, for example rheumatoid arthritis, osteoarthritis, osteopenias such as osteoporosis, periodontitis, gingivitis, corneal epidermal or gastric ulceration, and tumour metastasis, invasion and growth. It has been found that hydroxamic acid MMP inhibitors can also inhibit the production of the cytokine tumour necrosis factor ("TNF"). Compounds which inhibit the production or action of TNF are considered potentially useful for the treatment or prophylaxis of many inflammatory, infectious, immunological or malignant diseases. These include, but are not restricted to, septic shock, haemodynamic shock and sepsis syndrome, post ischaemic reperfusion injury, malaria, Crohn's disease, mycobacterial infection, meningitis, psoriasis, congestive heart failure, fibrotic disease, cachexia, graft rejection, cancer, autoimmune disease, rheumatoid arthritis, multiple sclerosis, radiation damage, toxicity following administration of immunosuppressive monoclonal antibodies such as OKT3 or CAMPATH-1 and hyperoxic alveolar injury.

Metalloproteinases are characterised by the presence in the structure of a zinc(II) ionic site. It is now known that there exists a range of metalloproteinase enzymes that includes fibroblast collagenase (Type 1), PMN-collagenase, 72 kDa-gelatinase, 92 kDa-gelatinase, stromelysin, stromelysin-2 and PUMP-1. Many known MMP inhibitors are peptide derivatives, based on naturally occuring amino acids, and are analogues of the cleavage site in the collagen molecule. Other known MMP inhibitors are less peptidic in structure, and may more properly be viewed as pseudopeptides or peptide mimetics. Such compounds usually have a functional group capable of binding to the zinc (II) site in the MMP, and known classes include those in which the zinc binding group is a hydroxamic acid, carboxylic acid, sulphydryl, and oxygenated phosphorus (eg phosphinic acid and phosphonamidate including aminophosphonic acid) groups.

Two known classes of pseudopeptide or peptide mimetic MMP inhibitors have a hydroxamic acid group and a carboxylic group respectively as their zinc binding groups. With a few exceptions, such known MMPs may be represented by the structural formula (A)

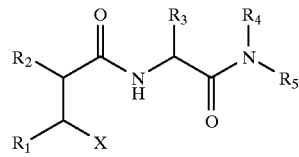

in which X is the zinc binding hydroxamic acid (—CONHOH) or carboxylic acid (—COOH) group and the groups $R_1$ to $R_5$ are variable in accordance with the specific prior art disclosures of such compounds.

A particular class of known MMP inhibitors is characterised by the presence of an allyl group in the $R_1$ position. Such compounds are disclosed, for example in WO 94/21625. That publication states that the preferred stereochemical configuration at the carbon atom carrying the allyl group is S and at the carbon atom carrying the $R_2$ group is R. It also states that the disclosed MMP inhibitors may be prepared by coupling an acid of formula (B) or an activated derivative thereof with an amine of formula (C):

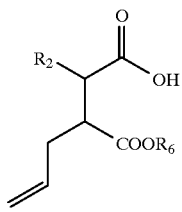

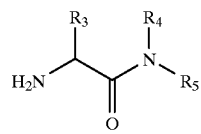

wherein $R_2$–$R_5$ are as defined in the publication, and $R_6$ represents an alkyl (eg t-butyl) or benzyl group, and if desired then converting the —$COOR_6$ group to a hydroxamic acid group.

BRIEF DESCRIPTION OF THE INVENTION

It follows from the above that compounds of type B and carboxylate variants thereof, particularly those having the stereochemical configuration referred to above, are useful intermediates for the preparation of the MMP inhibitors. This invention relates to a novel process for the preparation of such compounds, and to novel starting materials useful in such process.

The aliphatic Claisen rearrangement of allyl enol ethers has become one of the most powerful tools for stereocontrolled carbon-carbon bond formation (for recent reviews see P. Wipf in *Comprehensive Organic Synthesis*, Vol. 5 (Eds.: B. M. Trost, I. Fleming, L. A. Paquette) Pergamon, N.Y., 1991, p 827; S. Blechert, Synthesis, 1989, 71; F. E. Zeigler, Chem. Rev., 1988, 88, 1423). Among the available methods for effecting this [3,3] sigmatropic rearrangement is the Ireland-Claisen procedure by which a silyl ketene acetal of an allyl ester can be converted to an α-allyl carboxylic acid. A particularly important aspect of the Ireland Claisen rearrangement is that, through efficient control of ketene acetal geometry, a highly reliable transfer of stereochemistry from starting material to product can be realised (R. E. Ireland, P. Wipf and J. D. Armstrong, J. Org. Chem. 1991, 56, 650; ibid 56, 3572). The process of the present invention is based on the application of the Ireland-Claisen rearrangement to the synthesis of 2,3-disubstituted succinates

DETAILED DESCRIPTION OF THE INVENTION

According to the present invention there is provided a process for the preparation of a compound of formula (I):

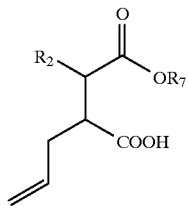

(I)

wherein $R_2$ is a $(C_1-C_6)$alkyl, $(C_2-C_6)$alkenyl, $(C_2-C_6)$ alkynyl, phenyl$(C_1-C_6)$alkyl, heteroaryl$(C_1-C_6)$alkyl, cycloalkyl$(C_1-C_6)$alkyl or cycloalkenyl$(C_1-C_6)$ alkyl group, any one of which may be optionally substituted by one or more substituents selected from $(C_1-C_6)$alkyl, —O$(C_1-C_6)$alkyl, —S$(C_1-C_6)$alkyl, halo and cyano (—CN); and $R_7$ is a carboxylic acid protecting group, which process comprises the internal molecular rearrangement of an allyl carboxylate compound of formula (II):

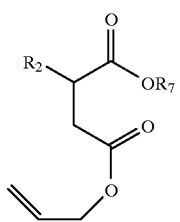

(II)

wherein $R_2$ and $R_7$ are as defined in relation to formula (I) to form the desired compound of formula (I).

It has been found that if the stereochemical configuration of the compound (II) is as shown in formula (IIA), then the resultant product of formula (I) contains the preferred diastereomer (IA) as a substantial and often preponderant proportion of the whole. Further enrichment or complete separation of the desired diastereomer may be effected by the usual methods of differential solubility or chromatography.

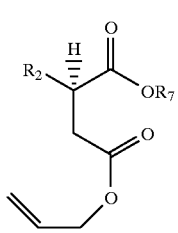

(IIA)

-continued

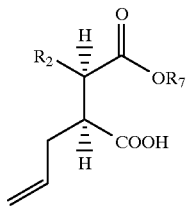

(IA)

In one convenient aspect of the invention, the rearrangement may be effected in an aprotic solvent such as tetrahydrofuran, by first converting the allyl ester II/IIA to the enol form, for example by treatment with a strong organic base, such as lithium diisopropylamine, followed by silylation of the enol hydroxy group, using a silylating agent (eg trimethylsilyl chloride, triethylsilyl chloride, tripropylsilyl chloride, tert-butyldimethylsilyl chloride, or tert-butyldiphenylsilyl chloride). The resultant silyl ketene acetal then undergoes the desired rearrangement to produce the readily hydrolysable silyl ester of compound I/IA. In the foregoing procedure, enolisation and silylation are preferably effected at low temperature, eg −70° C. or lower, and the rearrangement may be induced by raising the temperature, eg to about 4° C. to 55° C.

Carboxylic acid protecting groups $R_7$ are of course well known, eg from the art of peptide synthesis, and are discussed in the widely used handbook by T. W. Greene and P. G. M. Wuts, Protective groups in Organic Synthesis, 2nd Edition, Wiley, N.Y. 1991, and elsewhere in the chemical literature. Clearly the protecting group will be chosen from amongst those which are non-labile under the conditions for the internal rearrangement of compound (II)/(IIA). Specific examples of carboxylic acid protecting groups which should be suitable under most such conditions include allyl, tert-butyl, and benzyl, optionally substituted in the phenyl ring by one or more nitro or methoxy substituents, for example 4-methoxybenzyl or 2,4-dimethoxybenzyl.

The intermediates of formula (II)/(IIA) as defined and discussed above are novel structures in there own right, and constitute a further aspect of the present invention.

The group $R_2$ in compounds (II)/(IIA) will generally be predetermined by the intended MMP inhibitor for which compound (I)/(IIA) is the intermediate. In the above definition of the group $R_7$:

The term "$(C_1-C_6)$alkyl" or "lower alkyl" means a straight or branched chain alkyl moiety having from 1 to 6 carbon atoms, including for example, methyl, ethyl, n-propyl, isopropyl, n-butyl, isobutyl, sec-butyl, t-butyl, pentyl and hexyl.

The term "$(C_2-C_6)$alkenyl" means a straight or branched chain alkenyl moiety having from 2 to 6 carbon atoms at least one double bond of either E or Z stereochemistry where applicable. This term would include, for example, vinyl, allyl, 1- and 2-butenyl and 2-methyl-2-propenyl.

The term "cycloalkyl" means a saturated alicyclic moiety having from 3–8 carbon atoms and includes, for example, cyclohexyl, cyclooctyl, cycloheptyl, cyclopentyl, cyclobutyl and cyclopropyl.

The term "cycloalkenyl" means an unsaturated alicyclic moiety having from 3–8 carbon atoms and includes, for example, cyclohexenyl, cyclooctenyl, cycloheptenyl, cyclopentenyl, cyclobutenyl and cyclopropenyl. In the case of cycloalkenyl rings of from 5–8 carbon atoms, the ring may contain more than one double bond.

The unqualified term "heteroaryl" means a 5–7 membered substituted or unsubstituted aromatic heterocyclic ring, optionally fused to a benzene ring, including for example, pyridinyl, thienyl and furanyl.

Specific examples of the group $R_2$ include n-pentyl, n-hexyl, n-heptyl, n-octyl, n-nonyl, n-decyl, cyclohexylpropyl, phenylpropyl, 4-chlorophenylpropyl, 4-methylphenylpropyl, 4-methoxyphenylpropyl, phenylbutyl, propyloxymethyl, propylsulphanyl, and in particular isobutyl.

Compounds of formula (II)/(IIA) may be prepared by esterification of a compound of formula (III)/(IIIA) with allyl alcohol,

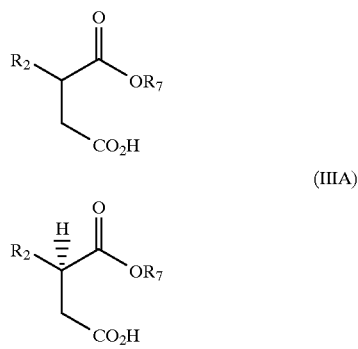

(III)

(IIIA)

$R_2$ and $R_7$ being as defined in relation to formula (I) above. Such esterification reaction may be assisted by the presence of a dehydrating agent such as a carbodiimide, eg N-ethyl-N'-(3-dimethylaminopropyl)carbodiimide hydrochloride in the presence of a catalytic amount of dimethylaminopyridine.

Compounds of formula (III)/(IIIA) are either known or are accessible by methods analagous to those used in the Examples herein.

The following Example 1 illustrates an embodiment of the process of the invention, and Example 2 illustrates the use of the product of that process as an intermediate in the preparation of a known MMP inhibitor.:

The following abbreviations have been used throughout:

DCM Dichloromethane

DMAP 4-Dimethyl-aminopyridine

DMF N,N-Dimethylformamide

EDC N-Ethyl-N'-(3-dimethylaminopropyl)carbodiimide hydrochloride

HOBt 1-Hydroxybenzotriazole

LIOH Lithium hydroxide monohydrate

MeOH Methanol

NMM N-methylmorpholine

TESCI Chlorotriethylsilane

TFA Trifluoroacetic acid

THF Tetrahydrofuran

TLC Thin layer chromatography $^1$H NMR spectra were recorded using a Bruker AC 250E spectrometer at 250.1 MHz.

EXAMPLE 1

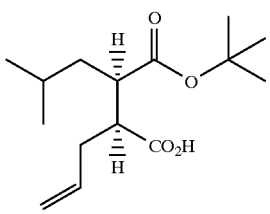

2S-Allyl-3R-isobutyl-succinic acid-4-tert-butyl ester (10:1, SR:RR)

Step A:

2-Benzyloxycarbonyl-3R-isobutyl-succinic acid 4-tert-butyl ester 1-benzyl ester

2-Benzyloxycarbonyl-3R-isobutyl-succinic acid benzyl ester (prepared by the method described in EP 0 446 267 ) (25.0 g, 62.8 mmol) was dissolved in diethyl ether (13 ml) and concentrated $H_2SO_4$ (0.66 ml) was added with stirring. The resulting solution was cooled to −78° C. and isobutylene gas was condensed into the reaction vessel until the volume had doubled. The reaction was allowed to warm slowly to room temperature and stirred overnight. The reaction mixture was poured into a mixture of sodium hydroxide (9 g, 0.225 mol), ice (32 g) and water (32 ml). The layers were separated and the aqueous layer further extracted with diethyl ether. The organic extracts were combined, dried and concentrated under reduced pressure to give a clear oil. This was purified by column chromatography (silica gel, dichloromethane) to provide the title compound as an oil which crystallised on standing (14.6 g, 51%). δ ($CDCl_3$), 7.32 (10H, s), 5.15 (4H, m), 3.79 (1H, d, J=10.2 Hz), 3.11 (1H, ddd, J=10.3, 4.3, 4.3 Hz), 1.69–1.52 (2H, m),1.43 (9H, s), 1.19–1.07 (1H, m), 0.89–0.84 (6H, m).

Step B:

2-Carboxy-3R-isobutyl-succinic acid 4-tert-butyl ester

The product from step A (22.8 g, 50.0 mmol) was dissolved in ethanol (300 ml) and the solution was placed under a blanket of argon. 10% Palladium on charcoal (3.2 g) was added and a fine stream of hydrogen gas was passed through the suspension for 15 min and then the solution was left under an atmosphere of hydrogen gas overnight with stirring. TLC showed that all the starting material had been consumed. The system was purged with argon and the catalyst was removed by filtration. Solvent was evaporated to give the desired product (13.7 g, 100%). δ ($CDCl_3$), 9.96 (2H, bs), 3.71–3.68 (1H, m), 3.11–3.02 (1H, m), 1.68–1.56 (2H, m), 1.43 (9H, s), 1.35–1.21(1H, m), 0.95–0.88 (6H, m).

Step C:

3R-isobutyl-succinic acid-4-tert-butyl ester

The product from step B (13.7 g 50.0 mmol) was dissolved in toluene (200 ml) and resulting solution was heated at reflux for 4 h. The reaction was cooled to room temperature and the solvent removed under reduced pressure to give the desired product as a colourless oil (10.1 g, 88%). δ ($CDCl_3$), 11.58 (1H, bs), 2.76–2.57 (2H, m), 2.39 (1H, dd, J=16.0, 4.4 Hz), 1.63–1.51 (2H, m), 1.42 (9H, s), 1.28–1.21 (1H, m), 0.92(3H, d, J=6.4 Hz), 0.88 (3H, d, J=6.4 Hz).

Step D:

2R-isobutyl-succinic acid 4-allyl ester 1-tert-butyl ester

The product from Step C (10.0 g, 43.0 mmol) was dissolved in DMF (100 ml) and EDC (9.99 g, 52.0 mmol), DMAP (catalytic) and allyl alcohol (3 ml, 45.0 mmol) were added with stirring. The reaction mixture was stirred at room temperature overnight. The solvent was removed under reduced pressure and the residue was taken up in ethyl acetate and washed successively with 1M HCl, 1 M Na$_2$CO$_3$, brine, dried and concentrated under reduced pressure to give the desired product as a colourless oil (9.3 g, 80%). δ (CDCl$_3$), 5.92–5.79 (1H, m), 5.32–5.16 (2H, m), 4.55–4.52 (2H, m), 2.78–2.69 (1H, m), 2.62 (1H, dd, J=16.0, 9.3 Hz), 2.35 (1H, dd, J=16.0, 5.0 Hz), 1.61–1.46 (2H, m), 1.40 (9H, s), 1.26–1.14 (1H, m), 0.90 (3H, d, J=6.5 Hz), 0.86 (3H, d, J=6.5 Hz).

Step E:

2S-Allyl-3R-isobutyl-succinic acid-4-tert-butyl ester (10:1, SR:RR)

To a stirred solution of diisopropylamine (0.3 ml, 2.21 mmol) in dry THF (10 ml) under an argon atmosphere at −70° C. was slowly added butyllithium (1.3 ml, 2.02 mmol, 1.6M solution in hexanes). The solution was warmed to −30° C. and stirred for 10 min and then cooled back to −70° C. A solution of 2R-isobutyl-succinic acid 4-allyl ester 1-tert-butyl ester (500 mg, 1.84 mmol) in dry THF (5 ml) was added and the reaction stirred for 30 min at −70° C. and TESCI (0.6 ml) added. After a further 5 min at −70° C. the reaction was warmed to 4° C. and left at this temperature for 3 days. Methanol (7 ml) was added and solvent was removed under reduced pressure. The residue was taken up in ethyl acetate and washed successively with 1M citric acid and brine. The aqueous layer was further extracted with ethyl acetate and the combined organic extracts were dried and concentrated to give a pale yellow oil. This was purified by column chromatography (silica gel, gradient elution, 0–4% methanol in dichloromethane) to afford the title compound as a yellow oil (276 mg, 55%). δ (CDCl$_3$), 5.83–5.67 (1H, m), 5.09–4.99 (2H, m), 2.66–2.59 (2H, m), 2.41–2.22 (2H, m), 1.71–1.47 (2H, m), 1.44 (8.2H, s), 1.41 (0.8H, s), 1.19–1.09 (1H, m), 0.89 (3H, d, J=2.7 Hz), 0.87 (3H, d, J=2.7 Hz).

The above intermediate can be used to prepare matrix metalloproteinase inhibitors, such as those described in WO 94/21625, by methods as described in example 2 using the appropriate starting materials.

EXAMPLE 2

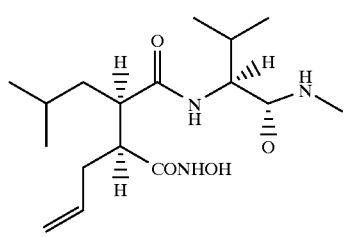

2S-Allyl-N 4-(2,2-dimethyl-1-methyl carbamoyl-propyl)-N 1-hydroxy-3R-isobutyl-succinamide Step A:

2S-Allyl-3R-isobutyl-succinic acid-1-tert-butyl ester 4-methyl ester

A solution of 2S-Allyl-3R-isobutyl-succinic acid-4-tert-butyl ester (10:1, SR:RR) (3.50 g, 13.0 mmol) in DCM was treated with diazomethane (generated by the procedure described in Chemistry & Industry, 708, 1990) to yield the desired product as a yellow oil (3.08 g, 83%). δ (CDCl$_3$), 5.78–5.61 (1H, m), 5.27–4.96 (2H, m), 3.64 (2.7H, s), 3.63 (0.3H, s), 2.70–2.55(2H, m), 2.38–2.19 (2H, m), 1.68–1.46 (2H, m), 1.43 (8.2H,. s), 1.40 (0.8H, s), 1.23–0.97 (1H, m), 0.87 (3H, d, J=3 Hz), 0.85 (3H, d, J=3 Hz).

Step B:

2S-Allyl-3-R-isobutyl-succinic acid 4-methyl ester

The product from step A (3.08 g, 10.8 mmol) was treated a solution of TFA/DCM (20 ml of each) at 4° C. overnight. The solvents were removed under reduced pressure. Residual TFA was removed by toluene azeotrope (×3) and the resulting oil was triturated with ether to give the product as a pale yellow foam (2.37 g, 96%).δ (CDCl$_3$), 10.81 (1H, bs), 5.80–5.63 (1H, m), 5.13–5.00 (2H, m), 3.69 (3h, s), 2.81–2.71 (2H, m), 2.47–2.24 (2H, m), 1.73–1.54 (2H, m), 1.18–1.09 (1H, m), 0.90 (6H, d, J=6.5 Hz).

Step C:

2S-[1-(2,2-dimethyl-1-methyl carbamoyl-propyl carbamoyl)-3R-methyl-butyl]-pent-4-enoic acid methyl ester To a stirred solution of 2S-Allyl-3 R-isobutyl-succinic acid 4-methyl ester (2.37 g, 10.0 mmol) in EtOAc (50 ml) was added HOBt (1.40 g, 10.0 mmol), EDC (1.90 g, 10.0 mmol), tert-leucine N-methylamide(1.80 g, 12.0 mmol) and NMM (1.1 ml, 10.0 mmol). The resulting mixture was heated at reflux overnight. After cooling to room temperature the mixture was washed with 1 M HCl, sat sodium bicarbonate solution and brine, dried and the solvent removed under reduced pressure yield the desired product as a yellow solid (2.90 g, 82%). δ (CDCl$_3$), 7.26 (1 H, m), 6.88 (1 H, d, J=9.4 Hz), 5.78–5.62 (1H, m), 5.06–4.97 (2H, m), 4.50 (0.9H, d, J=9.4 Hz), 4.42 (0.1H, d, J=9.4Hz), 3.66 (2.7H, s), 3.65 (0.3, s), 2.76 (3H, d, J=4.7 Hz), 2.73–2.55 (1H, m), 2.38–2.26 (1H, m), 1.63–1.54 (1H, m), 1.51–1.31 (1H, m), 1.12–1.03 (1H, m), 0.99 (7.8H, s), 0.97 (1.1H, s), 0.81 (3H, d, J=6.5 Hz), 0.77 (3H, d, J=6.6 Hz).

Step D:

2S-Allyl-N 4-(2,2-dimethyl-1-methyl carbamoyl-propyl)-N 1-hydroxy-3R-isobutyl-succinamide The product from Step C (2.90 g, 8.18 mmol) was dissolved with stirring in a solution of THF(30 ml) and water (30 ml). LIOH (514 mg, 12.27 mmol) was added and stirring was continued at room temperature for 3 days. The reaction was quenched with 1 M HCl and concentrated under reduced pressure. The solution was extracted with EtOAc (×3). The organic extracts were combined, dried and evaporated to dryness under reduced pressure. The resulting pale yellow solid was purified by column chromatography, eluting with 50% hexane in EtOAc then 100% EtOAc to give 2S-[1-(2,2dimethyl-1-methyl carbamoyl-propyl carbamoyl)-3R-methyl-butyl]-pent-4enoic acid as a yellow foam. This was converted directly into the hydroxamic acid as follows: 2S-[1-(2,2-dimethyl-1-methyl carbamoyl-propyl carbamoyl)-3R-methyl-butyl]-pent-4-enoic acid (1.86 g, 5.46 mmol) was taken up in DMF (25 ml) and HOBt (886 mg, 6.56 mmol) and EDC (1.30 g, 6.56 mmol) added. The resulting mixture stirred at room temperature for 2 h. A solution of hydroxylamine hydrochloride (569 mg, 8.19 mmol) and NMM (0.9 ml, 8.19 mmol) in DMF (5 ml) was added and the mixture stirred at room temperature overnight. The solvent was removed under reduced pressure. The resulting residue was purified by column chromatography on acid washed silica, eluting with 2% MeOH in DCM to yield the product as a white foam. The $^1$H nmr was in accordance with that quoted previously in WO 94/21625.

We claim:
1. A process for the preparation of a compound of formula (I):

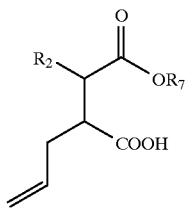
(I)

wherein $R_2$ is a $(C_1-C_6)$alkyl, $(C_2-C_6)$alkenyl, $(C_2-C_6)$alkynyl, phenyl$(C_1-C_6)$alkyl, heteroaryl$(C_1-C_6)$alkyl, cycloalkyl$(C_1-C_6)$alkyl or cycloalkenyl$(C_1-C_6)$ alkyl group, any one of which may be optionally substituted by one or more substituents selected from $(C_1-C_6)$alkyl, —O$(C_1-C_6)$alkyl, —S$(C_1-C_6)$alkyl, halo and cyano (—CN); and $R_7$ is a carboxylic acid protecting group, which process comprises the internal molecular rearrangement of an allyl carboxylate compound of formula (II):

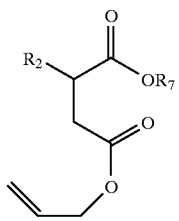
(II)

wherein $R_2$ and $R_7$ are as defined in relation to formula (I) to form the desired compound formula (I).

2. A process as claimed in claim 1 wherein the stereochemical configuration of the compound (II) is as shown in formula (IIA), and the resultant product of formula (I) is isolated as a diastereomer of formula (IA):

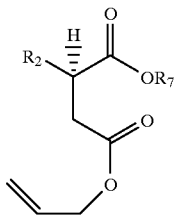
(IIA)

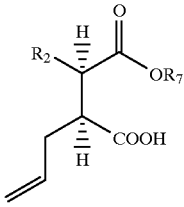
(IA)

3. A process as claimed in claim 1 or claim 2 wherein the rearrangement is effected in an aprotic solvent, by first converting the allyl ester II/IIA to the enol form, followed by silylation of the enol hydroxy group, allowing or inducing the rearrangement of the resultant silyl ketene acetal, then hydrolysing the resultant silyl ester of compound I/IA.

4. A process as claimed in claim 3 wherein the enolisation and silylation are effected at about −70° C. or lower, and the rearrangement is induced by raising the temperature to about 4° C. to about 55° C.

5. A compound of formula (II) or (IIA) as defined in claim 1 or claim 2.

6. A process as claimed in any of claim 1 wherein the carboxylic acid protecting group $R_7$ is allyl, tert-butyl, or benzyl which may be optionally substituted in the phenyl ring by one or more nitro or methoxy substituents.

7. A process as claimed in claim 1 wherein $R_2$ is n-pentyl, n-hexyl, n-heptyl, n-octyl, n-nonyl, n-decyl, cyclohexylpropyl, phenylpropyl, 4-chlorophenylpropyl, 4-methylphenylpropyl, 4-methoxyphenylpropyl, phenylbutyl, propyloxymethyl, propylsuphanyl, or isobutyl.

8. A compound as claimed in claim 5 wherein the carboxylic acid protecting group $R_7$ is allyl, tert-butyl, or benzyl which may be optionally substituted in the phenyl ring by one or more nitro or methoxy substituents.

9. A compound as claimed in claim 5 wherein $R_2$ is n-pentyl, n-hexyl, n-heptyl, n-octyl, n-nonyl, n-decyl, cyclohexylpropyl, phenylpropyl, 4-chlorophenylpropyl, 4-methylphenylpropyl, 4-methoxyphenylpropyl, phenylbutyl, propyloxymethoxy, propylsulphanyl, or isobutyl.

* * * * *